United States Patent
Barrier et al.

(10) Patent No.: US 9,039,714 B2
(45) Date of Patent: May 26, 2015

(54) DEVICE TO ASSIST DELIVERY OF FETAL HEAD AT CESAREAN SECTION

(75) Inventors: Breton F. Barrier, Columbia, MO (US); Gary F. Clark, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 411 days.

(21) Appl. No.: 13/016,057

(22) Filed: Jan. 28, 2011

(65) Prior Publication Data

US 2011/0196382 A1    Aug. 11, 2011

Related U.S. Application Data

(60) Provisional application No. 61/337,695, filed on Feb. 5, 2010.

(51) Int. Cl.
*A61B 17/42* (2006.01)
*A61B 17/44* (2006.01)

(52) U.S. Cl.
CPC .................... *A61B 17/442* (2013.01)

(58) Field of Classification Search
CPC ...... A61B 17/42; A61B 17/442; A61M 31/00
USPC .............. 604/19, 48, 279; 606/119, 121, 122, 606/123
See application file for complete search history.

(56) References Cited

U.S. PATENT DOCUMENTS

| 1,338,464 | A | * | 4/1920 | Shafer ........................... 604/279 |
| 5,395,379 | A | * | 3/1995 | Deutchman et al. .......... 606/123 |
| 5,693,058 | A | * | 12/1997 | Cavanagh et al. ............. 606/123 |
| 2007/0043388 | A1 | * | 2/2007 | Greenwood .................. 606/193 |

FOREIGN PATENT DOCUMENTS

WO    2006085045    8/2006

* cited by examiner

*Primary Examiner* — Ashley Fishback
(74) *Attorney, Agent, or Firm* — Polster Lieder

(57) ABSTRACT

In various cases, an obstetrical device is provided for assisting a cesarean section delivery of a neonate having a fetal presenting part well seated within the mother's pelvis. Generally, the device comprises a tubular tail having an internal lumen and a hollow head extending from a distal end of the tail and having an internal chamber fluidly connected to the lumen. The head includes at least one aperture extending through an exterior wall. The device is operable to position the head near or in contact with the fetal presenting part to provide air into an area near and/or between contact surfaces of the fetal presenting part and a vagina and/or a cervix of the mother. Providing the air will reduce or release a suction formed between the contact surfaces such that the well seated fetal presenting part can be easily separated from the vagina and/or the cervix.

19 Claims, 9 Drawing Sheets

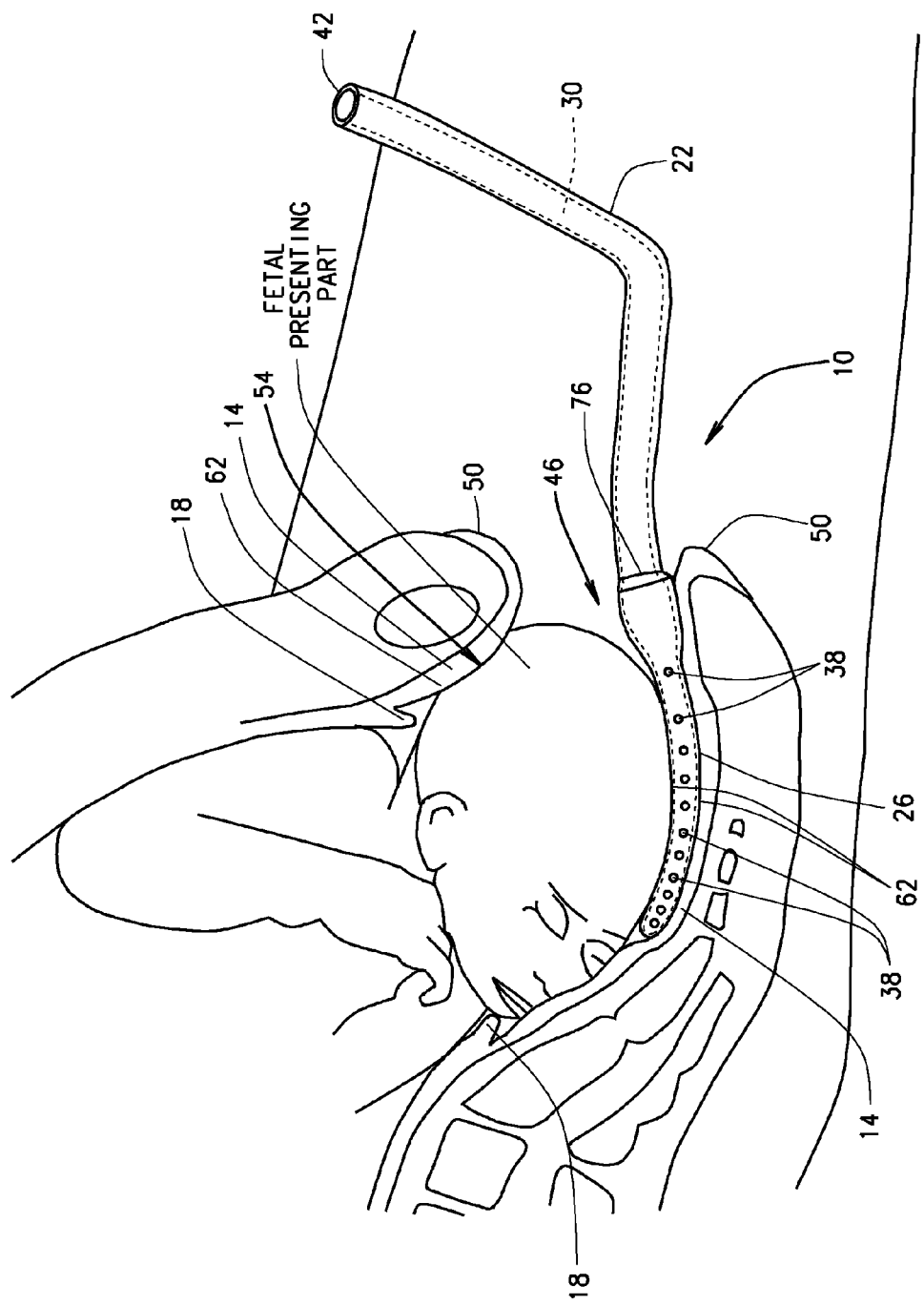

DEVICE TO ASSIST DELIVERY OF FETAL HEAD AT CESAREAN SECTION

CROSS-REFERENCE TO RELATED APPLICATIONS

This application claims the benefit of U.S. Provisional Application No. 61/337,695, filed on Feb. 5, 2010.

FIELD

The present disclosure relates to an obstetric device for assisting in the birth of a child, more specifically to an obstetric device to assist in the delivery of the fetal presenting part (head or breech) during cesarean section.

BACKGROUND

The statements in this section merely provide background information related to the present disclosure and may not constitute prior art.

In some instances complications may occur when a fetal presenting part (head or breech) is 'well applied' within the mother's pelvis during a cesarean delivery. The incidents are more common when a cesarean delivery is pursued after a natural birthing process is tried unsuccessfully. Since the patient/mother has labored, sometimes the fetal presenting part is well seated in the pelvis and the molding and caput of the head occupy the entirety of the potential space of the pelvic cavity. Particularly, the vagina and cervix are well applied to the head in a very wet environment, and digital or manual extraction from this environment places a large amount of suction on the fetal head, usually causing significant resistance to elevation of the head up through the uterine incision.

Common practice is for a surgical assistant to place his or her hand into the vagina and push up on the fetal presenting part while the surgeon attempts to gain leverage on the presenting part from the surgical field. Often, when the presenting part finally breaks the seal, a large sucking sound is heard as vaginal air and fluids are expelled up into the uterus and surrounding operative field. The force required to accomplish this may be excessive, and may lead to complications such as clavicle fracture of the neonate, tearing and extension of the lower uterine segment incision with significant blood loss, and rarely, skull fracture or inability to deliver the fetus resulting in fetal death.

SUMMARY

The present disclosure provides an obstetrical device, and methods of using the obstetrical device, for assisting a cesarean section delivery of a neonate having a fetal presenting part well seated within the mother's pelvis.

In various cases, the device comprises a hollow tail having an internal lumen extending the length of the tail. The device additionally comprises a hollow head extending from a distal end of the tail. The head includes at least one aperture extending through an exterior wall of the head, wherein the wall defines an internal chamber of the head that is fluidly connected to the tail internal lumen. The head is structured and operable to be inserted into a vaginal opening of the mother and positioned near or in contact with the fetal presenting part such that air is provided to, via the tail internal lumen, the head internal chamber and the at least one aperture of the head, into an area near and/or between contact surfaces of the fetal presenting part and a vagina and/or a cervix of the mother. The air provided allows suction formed between the contact surfaces to be reduced or released so that the well seated fetal presenting part can be easily separated from the vagina and/or the cervix.

In various other cases, the device comprises a hollow tail having an internal lumen extending the length of the tail. The device additionally includes a hollow head extending from a distal end of the tail, wherein the head includes at least one aperture extending through an exterior wall of the head. The wall defines an internal chamber of the head that is fluidly connected to the tail internal lumen. The head is structured and operable to be inserted and advanced into a vaginal opening of the mother. The device further includes an insertion marker disposed on a distal end portion of the tail. The insertion marker is operable to indicate when the head has been advanced into the vaginal opening a desired distance, whereby the head is positioned near or in contact with the fetal presenting part such that air is provided, via the tail internal lumen, the head internal chamber and the at least one aperture of the head, into an area near and/or between contact surfaces of the fetal presenting part and a vagina and/or a cervix of the mother. The air provided allows a suction formed between the contact surfaces to be reduced or released so that the well seated fetal presenting part can be easily separated from the vagina and/or the cervix.

In yet other cases, the method comprises inserting a head of an obstetrical device into a vaginal opening of the mother, wherein the obstetrical device comprises a hollow tail having an internal lumen extending the length of the tail. The device additionally comprises the head, which extends from a distal end of the tail. The head is hollow and includes at least one aperture extending through an exterior wall of the head that defines an internal chamber of the head that is fluidly connected to the tail internal lumen. The method additionally includes positioning the head near or in contact with the fetal presenting part, and providing air, via the internal lumen of the tail, the internal chamber and the at least one aperture of the head, into an area near and/or between contact surfaces of the fetal presenting part and a vagina and/or a cervix of the mother. Providing the air into the area near and/or between contact surfaces reduces or releases a suction formed between the contact surfaces so that the well seated fetal presenting part can be easily separated from the vagina and/or the cervix.

BRIEF DESCRIPTION OF THE DRAWINGS

The drawings described herein are for illustration purposes only and are not intended to limit the scope of the present teachings in any way.

FIG. 6b is an illustration of the obstetrical device shown in FIG. 1, having the tail structured with a bend such that a distal end of the tail will be positioned away from unsanitary matter during use, in accordance with still other various cases of the present disclosure.

Corresponding reference numerals indicate corresponding parts throughout the several views of drawings.

DETAILED DESCRIPTION OF THE INVENTION

Figure 1:
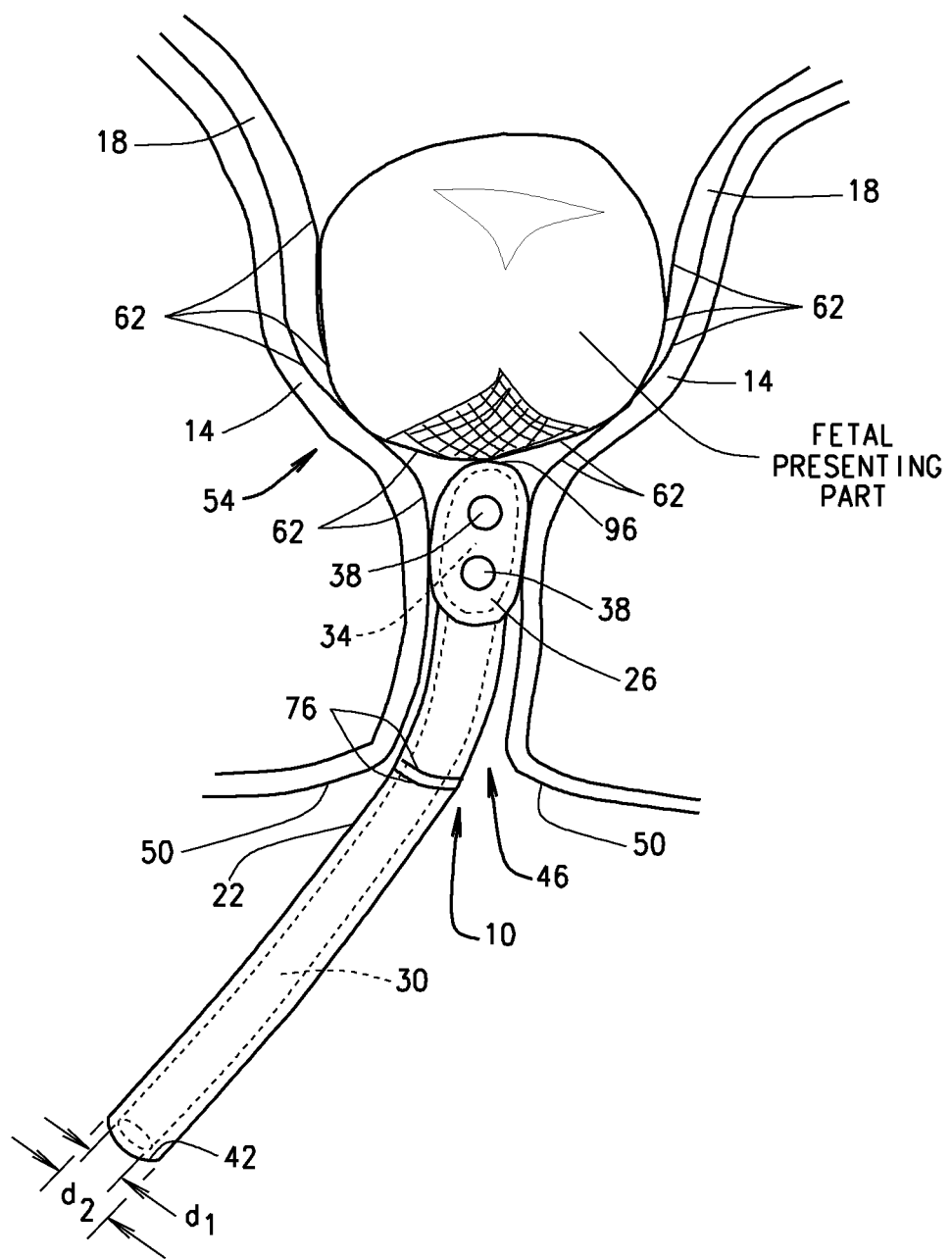
FIG. 1 is an illustration of an obstetrical device that is structured and operable to assist fetal presenting part delivery during a cesarean section, in accordance with various cases of the present disclosure.

The following description is merely exemplary in nature and is in no way intended to limit the present teachings, application, or uses. Throughout this specification, like reference numerals will be used to refer to like elements. Additionally, unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Referring to FIG. 1, in accordance with various cases, the present disclosure provides an obstetrical device 10, also referred to herein as the Cesarean Section Barrier Release Device (BRD) 10, that is structured and operable to assist in the cesarean section delivery of a neonate having a fetal presenting part (e.g., the head or breech of the neonate) well seated within the mother's pelvis. As used herein, the well seated presenting part means the presenting part that occupies the entirety of the potential space of the pelvic cavity 54 and is adhered to the vagina 14 and/or the cervix 18 of the mother via a suction formed between contact surfaces 62 of the fetal presenting part and the vagina 14 and/or cervix 18. More particularly, the BRD 10 is a device structured and operable to break the suction, i.e., significantly reduce or remove the suction, formed between a fetal presenting part (e.g., the head or breech of a neonate) and the vagina 14 and cervix 18 of a mother during a cesarean section.

The BRD generally includes a tail 22 and a head 26 extending from the tail 22. The head 26 can be integrally formed with the tail 22 or removably connectable to the tail 22. The tail 22 comprises a non-collapsible tubular, i.e., hollow, structure having an internal lumen 30, i.e., duct, cavity or passage, extending the length of the tail 22. The head 26 comprises a hollow, non-collapsible structure having an internal chamber 34 and includes one or more apertures 38 extending through an exterior wall of the head 26 that defines the internal chamber 34. Specifically, the internal lumen 30 of the tail 22 is fluidly connected to the internal chamber 34 of the head 26 and, hence, fluidly connected to the aperture(s) 38. And, the aperture(s) 38 is/are sized such that air can easily flow from a proximal end 42 of the tail, through the tail internal lumen 30 and the head internal chamber 34, and exit the head 26 through the aperture(s) 38.

As used herein, the term 'non-collapsible' should be understood to mean that the respective hollow, non-collapsible structure is fabricated, formed or constructed to be substantially non-collapsible when used as described herein. That is, the respective hollow, non-collapsible structure can be substantially rigid such that the respective cavity, chamber or lumen will not close or collapse during use, as described herein. Or, the respective hollow, non-collapsible structure can be flexible and can bend and flex during use, as described herein, but will not bend or flex such that the respective internal cavity, chamber or lumen of the hollow structure will close or collapse to a point where air cannot flow through the respective cavity, chamber or lumen.

Additionally, as used herein, the term 'tubular' should be understood to mean any elongated hollow structure having any suitable lateral cross-sectional shape, e.g., round, square, rectangular, triangular, oval, etc., and including an internal duct, cavity or passage, e.g., lumen 30, extending the length thereof and suitable for allowing air to flow therethrough.

Generally, in operation the head 26 is inserted into the mother's vaginal opening 46 and advanced until the head 26 is positioned near or in contact with the fetal presenting part that is well seated in the mother's pelvis. Once the head 26 is positioned near or in contact with the fetal presenting part, air will flow through the tail internal lumen 30, into the head internal chamber 34 and exit the head internal chamber 34, via the aperture(s) 38. Particularly, the air will flow into the area near and/or between the contact surfaces 62 where the suction is formed that is holding, or adhering, the fetal presenting part in contact with vagina 14 and/or the cervix 18. As described above, such suction or adhesion of the fetal presenting part with the vagina 14 and/or the cervix 18 can prevent easy delivery of the neonate.

More particularly, once the head 26 is positioned near or in contact with the fetal presenting part, the suction existing between the contact surfaces 62 will cause air to be drawn into the proximal end 42 of the tail 22. The air with then be drawn through the tail internal lumen 30, into the head internal chamber 34 and out through the apertures 38 into the area near and/or between the contact surfaces 62. Importantly, providing air into the area near and/or between the contact surfaces 62 will break the suction formed between a fetal presenting part and the vagina 14 and cervix 18 of the mother such that the fetal presenting part can be easily separated from the vagina 14 and/or cervix 18, thereby allowing easy delivery of the neonate.

As used herein, the phrase 'in contact with the fetal presenting part' should be understood to encompass positioning the BRD head 26 against the fetal presenting part that is exposed to the vaginal opening 46 and positioning the BRD head 26 against the fetal presenting part that is in contact with the vagina 14 and/or cervix 18, i.e., between the contact surfaces 62. For example, as exemplarily illustrated in FIG. 6*b*, since the mother is typically positioned on her back during delivery, in various implementations wherein the BRD head 26 is positioned between the contact surfaces 62, the head 26 could easily be positioned beneath, or under, the fetal presenting part between the contact surfaces 62.

The tail 22 can comprise any non-collapsible tubular device, rigid or flexible, that is suitable for use in a sterile surgical environment and is structured to provide sufficient air passage therethrough. For example, in various cases, the tail 22 can comprise a sterile non-collapsible tube, e.g., polyvinyl chloride (PVC), silicone or polyurethane tubing or any other suitable non-collapsible tubing. It is envisioned that the internal lumen 30 of tail 22 will have a diameter that is sufficiently large to allow air to flow unrestricted from the proximal end 42 to the head 26. For example, in various cases, the lumen 30 can have a diameter d1 between approximately 0.5 cm and approximately 2 cm, and the tail 22 can have an outer diameter d2 between approximately 0.7 cm and approximately 2.2 cm. Additionally, in various cases, the tail 22 is structured to have a length sufficient to allow the clinician to bend or flex the tail such that proximal end 42 is positioned away from any unsanitary matter near the vaginal opening 46 when the BRD 10 is being used. Alternatively, as described below with reference to FIG. 6*b*, the tail 22 can be structured to include a bend such the proximal end 42 will be positioned away any unsanitary matter near the vaginal opening 46 when the BRD 10 is being used.

As used herein, unsanitary matter includes unsanitary air, fluids or other biological matter that may collect near the vaginal opening 46 during the birthing process.

Similarly, the head 26 can comprise any hollow, non-collapsible structure that is suitable for use in a sterile surgical environment and is structured to provide sufficient air passage therethrough. For example, in various cases, the head 26 can be constructed from a medical-grade PVC, silicon or polyurethane based polymer, or any other suitable material or composite. Although the tail 22 is described herein as having a flexible structure, it is envisioned that in various other cases, the tail 22 can be fabricated from a generally rigid material that is similarly suitable for use in a sterile surgical environment.

In various cases, the BRD 10 can include an insertion marker 76 disposed on the distal end portion of the tail 22. The insertion marker 76 is operable to indicate when the BRD head 26 has been advanced into the vaginal opening 46 a desired distance such that the head 26 is positioned near and/or in contact with fetal presenting part. For example, in various implementations, the insertion marker 76 is disposed on the distal end portion of the tail 22 a predetermined length from a distal tip 96 of the head 26. The predetermined length is such that the head 26 will be positioned near and/or in contact with the fetal presenting part when a clinician has advanced the head 26 until the insertion marker 76 is substantially even with the labia 50 of the mother. At which point, it is envisioned that the suction will be significantly reduced or removed and the fetal presenting part can be easily separated from the vagina 14 and/or cervix 18, thereby allowing easy delivery of the neonate. The predetermined length can be any pragmatically defined length. For example, in various configurations, the insertion marker 76 can be disposed on the distal end portion of the tail 22 at a point that is between approximately 9 cm and 13 cm from the distal tip 96 of the head 26, e.g., 11 cm. The insertion marker 76 can be any marking of device affixed to or movably disposed on the tail 22, for example, a line printed on the tail 22 or an annular ring affixed to or movably disposed on the distal end portion of tail 22.

Figure 2A:
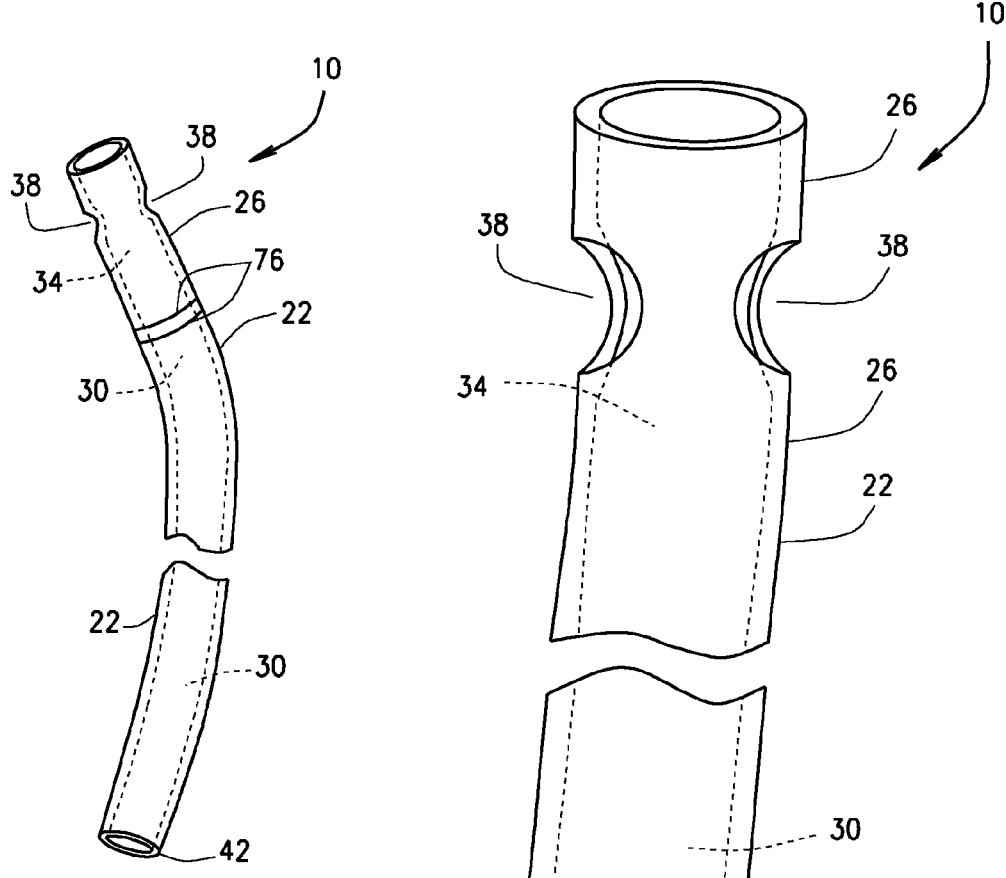
FIG. 2a is an illustration of the obstetrical device shown in FIG. 1, in accordance with various cases of the present disclosure.
Figure 2B:
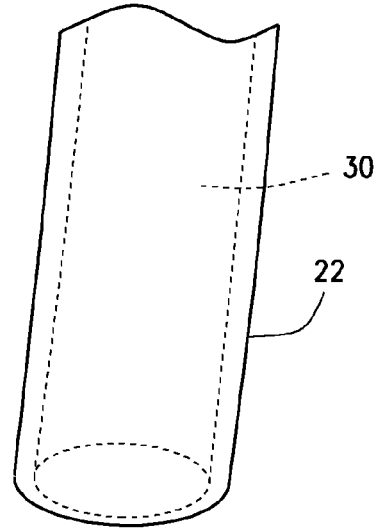
FIG. 2b is an enlarged view of the obstetrical device shown in FIG. 2a, in accordance with various cases of the present disclosure.
Figure 2C:
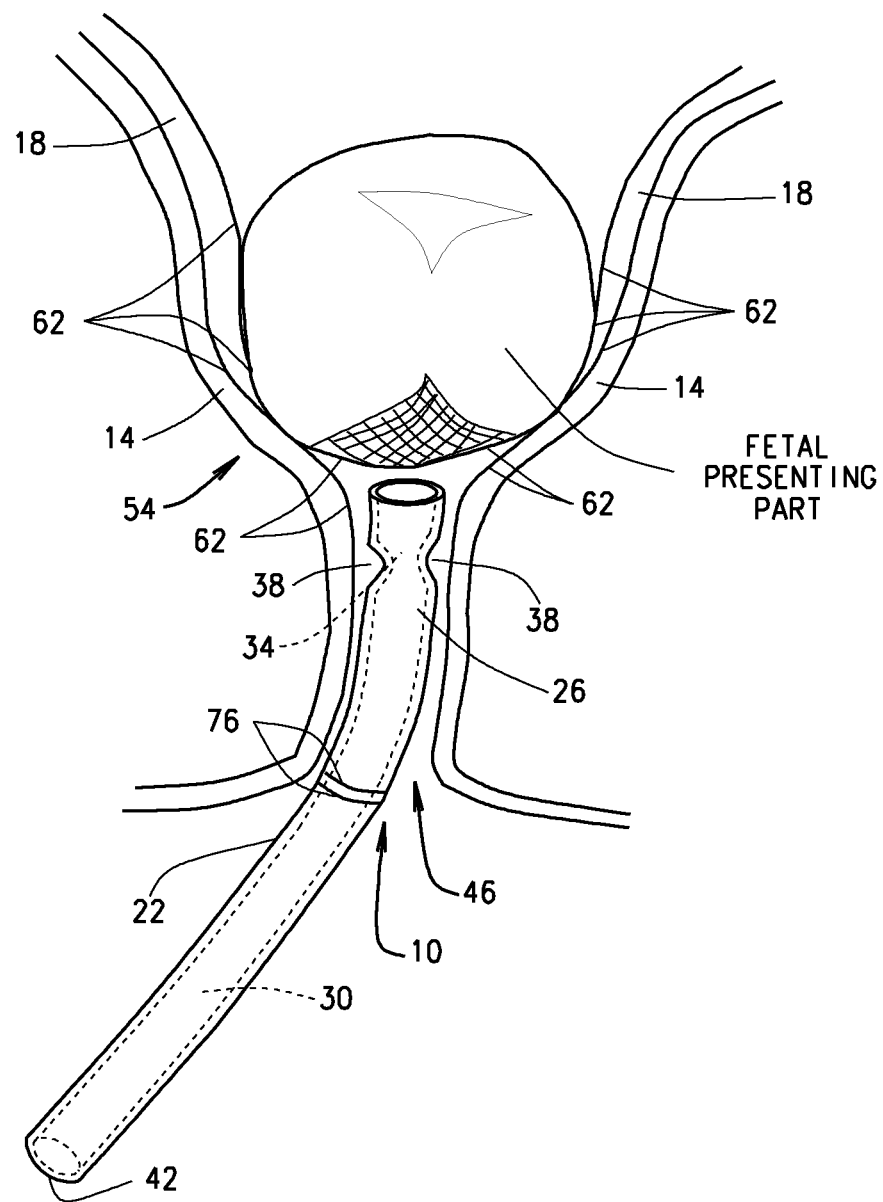
FIG. 2c is an illustration of utilization of the obstetrical device shown in FIGS. 2a and 2b, in accordance with various cases of the present disclosure.

Referring now to FIGS. 2*a*, 2*b* and 2*c*, in various cases, the head 26 can comprise an extension, or distal portion, of the tail 22 comprised of a sterile, non-collapsible tube, e.g., a medical-grade PVC, silicon or polyurethane based polymer, or any other suitable material or composite. In such cases, the aperture(s) 38 in the head 26 can comprise one or more holes extending through the sidewall of the head 26.

In such cases, to assist in delivery of the fetal presenting part during a cesarean section, the head 26 of BRD 10 is inserted into the vaginal opening 46 of a mother, with or without accompaniment of the clinician's hand. The head 26 is then advanced until the head 26 is adjacent or in contact with the fetal presenting part, e.g., until the insertion marker 76 is substantially even with the mother's labia 50. Once the head 26 is positioned adjacent or in contact with the fetal presenting part, the aperture(s) 38 allow air to flow from the proximal end 42 of the tail 22 to the area near the fetal presenting part and the vagina 14 and/or the cervix 18. This flow of air will penetrate between the contact surfaces 62 of fetal presenting part and the vagina 14 and/or the cervix 18, thereby breaking the suction, i.e., significantly reducing or removing the suction pressure, formed between the contact surfaces 62. Accordingly, once the suction is broken, the fetal presenting part can be easily removed from the pelvic cavity 54, and the neonate can be easily delivered through the cesarean opening.

Referring now to FIGS. 3*a* through 3*d*, in various cases, the head 26 can comprise a sterile, flexible, non-collapsible structure that is detachably coupled to, or substantially permanently affixed to, a distal end 58 of the tail 22. For example, in various implementations of such cases, the head 26 can comprise a flared hollow abutment portion 66 and a hollow neck portion 70 that define the internal chamber 34. The neck portion 70 is connectable to the distal end 58 of the tail 22. As described above, the head 26 can be integrally formed with the tail 22 or removably connectable to the tail 22, e.g., the neck portion 70 can be detachably connectable to, or substantially permanently affixed to, the distal end 58 of the tail 22.

Figure 3A:
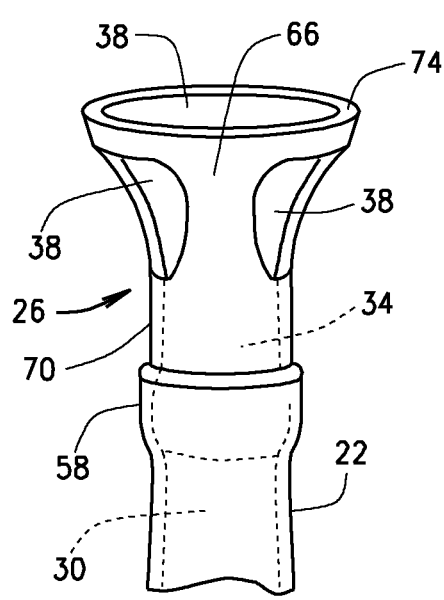
FIG. 3a is a side view of a head of the obstetrical device shown in FIG. 1, in accordance with various cases of the present disclosure.
Figure 3C:
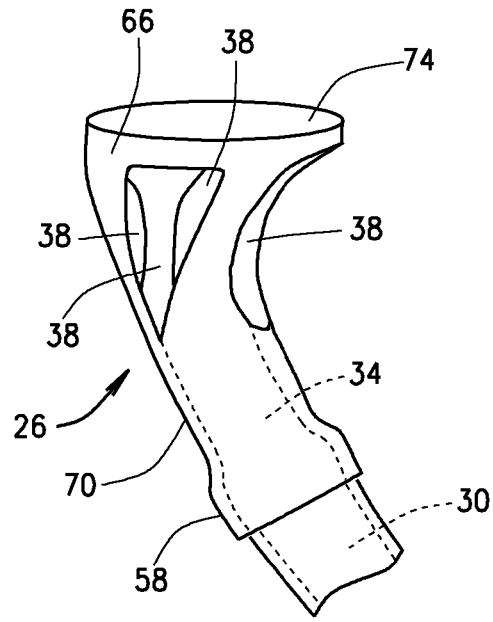
FIG. 3c is a side view of a head of the obstetrical device shown in FIG. 1, in accordance with various other cases of the present disclosure.
Figure 3B:
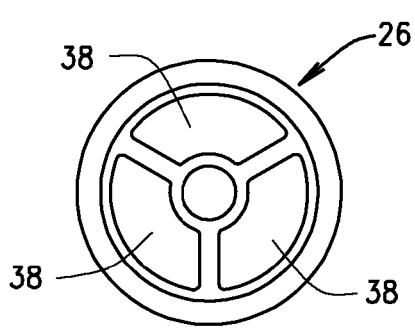
FIG. 3b is a top view of the head shown in FIG. 3a, in accordance with various cases of the present disclosure.
Figure 3D:
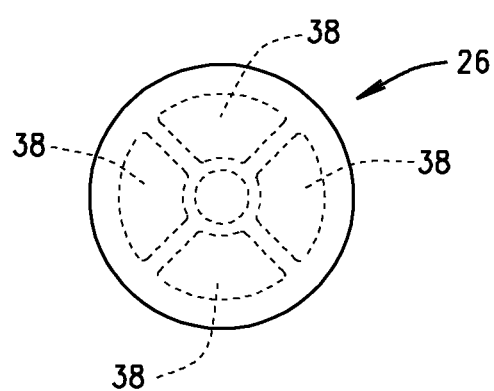
FIG. 3d is a top view of the head shown in FIG. 3c, in accordance with various cases of the present disclosure.
Figure 3E:
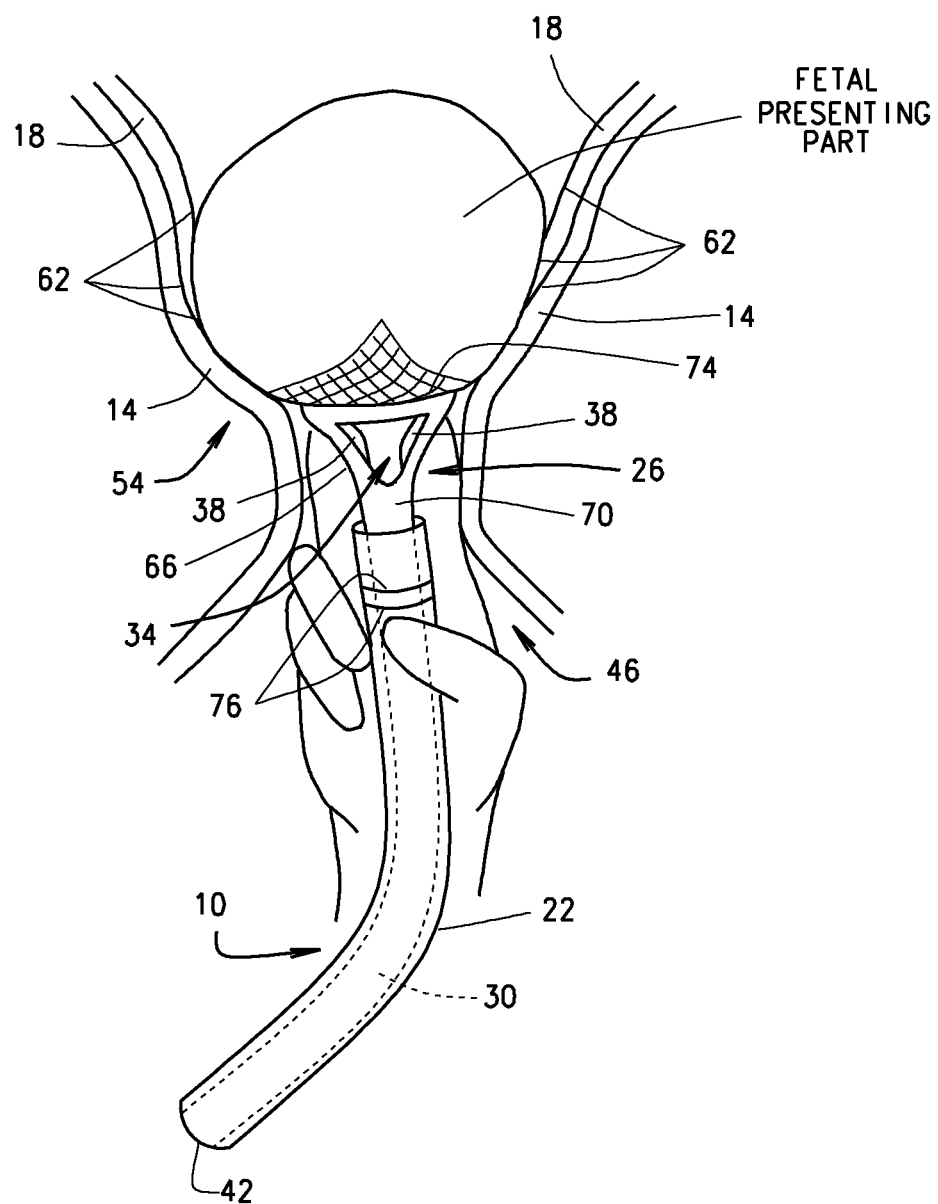
FIG. 3e is an illustration of utilization of the obstetrical device shown in FIGS. 3a, 3b, 3c and 3d, in accordance with various cases of the present disclosure.

As exemplarily illustrated in FIGS. 3*a* and 3*b*, in various cases it is envisioned that the abutment portion 66 can extend substantially straight from neck portion 70. Additionally, as exemplarily illustrated in FIGS. 3*c* and 3*d*, in various cases it is envisioned that the abutment portion 66 can extend in an angled manner or orientation from the neck portion 70 such that the head 26 is ergonomically structured to provide ease and comfort in holding by the clinician during the insertion. Furthermore, in various cases, it is envisioned that a distal face 74 of the abutment portion 66 can include one of a plurality of the apertures 38, as exemplarily illustrated in FIGS. 3*a* and 3*b*, while in other cases the abutment portion distal face 74 can be closed, e.g., concave, as exemplarily illustrated in FIGS. 3*c* and 3*d*. Importantly, the distal face 74 of the abutment portion 66 is structured to provide a safe and comfortable contact surface to the fetal presenting part.

As described above, in various cases the head 26 can include a plurality of apertures 38. For example, as illustrated in FIGS. 3*a* through 3*d*, the head 26 can include a plurality of apertures 38 disposed in the sidewall of the head 26. The size and shape of the apertures 38 may vary, as long as the apertures 38 provide sufficient air passage while maintaining the structure integrity of the head 26. Additionally, although FIGS. 3a through 3d exemplarily illustrate the head 26 as having a substantially round distal face 74, it is envisioned that the head 26 can be structured to have a distal face 74 of any shape suitable for positioning near or in contact with the fetal presenting part, as described above. For example, it is envisioned that the head 26 can be structured to have a substantially oval, or any other suitable shape, distal face 74.

With reference now to FIGS. 3a, 3b, 3c, 3d and 3e, to use the BRD 10 to assist in the delivery of the fetal presenting part during a cesarean section, the head 26 is inserted into the vaginal opening 46 of a mother, with or without accompaniment of the clinician's hand. The head 26 is then advanced until the distal face 74 of the abutment portion of the head 26 is placed near or in contact with the fetal presenting part, e.g., until the insertion marker 76 is substantially even with the mother's labia 50. Once the distal face 74 is place near or in contact with the fetal presenting part, the apertures 38 allow air to flow from the proximal end 42 of the tail 22 to the contact area between contact surfaces 62. This flow of air will penetrate between the contact surfaces 62, thereby breaking the suction, i.e., significantly reducing or removing the suction pressure, formed between the contact surfaces 62. Accordingly, once the suction is broken, the fetal presenting part can be easily removed from the pelvic cavity 54, and the neonate can be easily delivered through the cesarean opening.

Referring now to FIGS. 4a, 4b, 4c, 4d and 4e, in yet other cases, the head 26 can comprise a tongue-like device having a front face 78, a back face 82, and opposing sides 86. In such cases, the head 26 includes a plurality of the apertures 38 arrayed within the front and back faces 78 and 82. The sides 86 can also include a plurality of the apertures 38. Additionally, in such cases, the head 26 includes a hollow septum portion 90 and a neck portion 94 that define the head internal chamber 34. The neck portion 94 is connectable to tail 22. As described above, the head 26 can be integrally formed with the tail 22 or removably connectable to the tail 22, e.g., the neck portion 94 can be detachably connectable to, or substantially permanently affixed to, the distal end 58 of the tail 22. As described above, the head 26 generally comprises a hollow, non-collapsible structure. More particularly, the head 26 can be constructed of any non-collapsible flexible material that is suitable for medical use, for example a medical-grade PVC, silicon or polyurethane based polymer, or any other suitable material or composite.

Referring briefly to FIGS. 3a, 3c, 4a, 4b, 4c, 4d and 4e, as exemplarily illustrated in FIGS. 3c, 4a, 4d and 4e, it is envisioned that in various cases the neck portion can be structured to fit over the external circumference of the tail distal end 58. Or, alternatively, in various cases, the neck portion can be structured to fit within the internal lumen 30 of the tail 22, as exemplarily illustrated in FIGS. 3a, 4b and 4c.

Referring again to FIGS. 4a, 4b, 4c, 4d and 4e, in various cases, the septum portion 90 has a curvature such that the front face 78 is slightly concave, while the back face 82 is slightly convex. The curvature of the septum portion 90 can have any degree β of curvature that is conducive to insertion of the head 26 between the contact surfaces 62 of the fetal presenting part and the vagina 14 and/or the cervix 18, as described below. For example, in various implementations, the degree β of curvature can be between 10° and 40°, e.g., 30°. Additionally, in various cases, the thickness of the septum portion 90 can be slightly tapered from a neck end 92 of the septum portion 90 to the distal end 93 of the septum portion 90. The thickness of the septum portion 90 can have any amount of tapering that is conducive to insertion of the head 26 between the contact surfaces 62, as described below, and allows the internal chamber 34 to remain open, i.e., not collapsed, after such insertion. For example, in various implementations, the neck end 92 can have a thickness T1 of approximately 1 cm and the distal end can have thickness T2 of 0.75 cm.

Figure 4D:
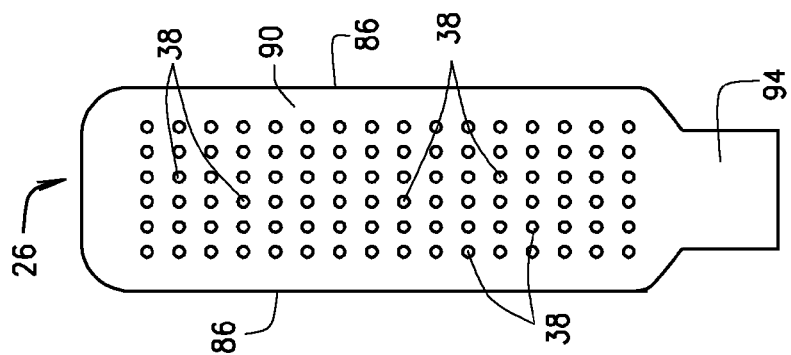
FIG. 4d is a front view of a head of the obstetrical device shown in FIG. 4c, in accordance with various other cases of the present disclosure.
Figure 4C:
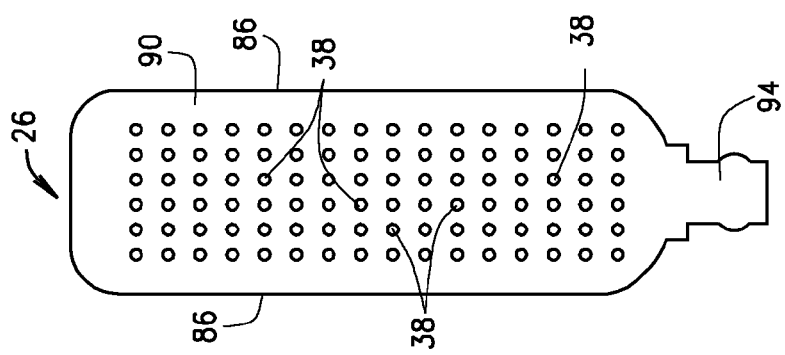
FIG. 4c is a front view of a head of the obstetrical device shown in FIG. 4a, in accordance with yet other various cases of the present disclosure.
Figure 4B:
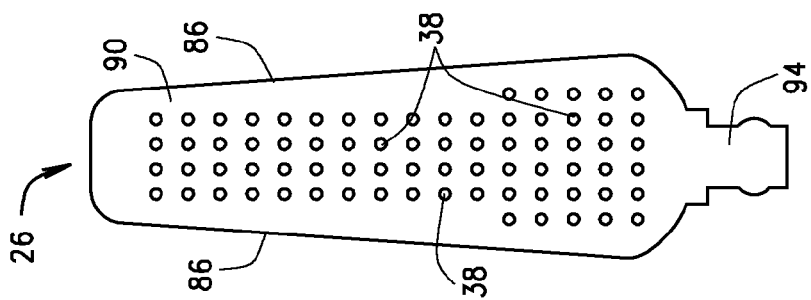
FIG. 4b is a front view of a head of the obstetrical device shown in FIG. 4a in accordance with various other cases of the present disclosure.
Figure 4A:
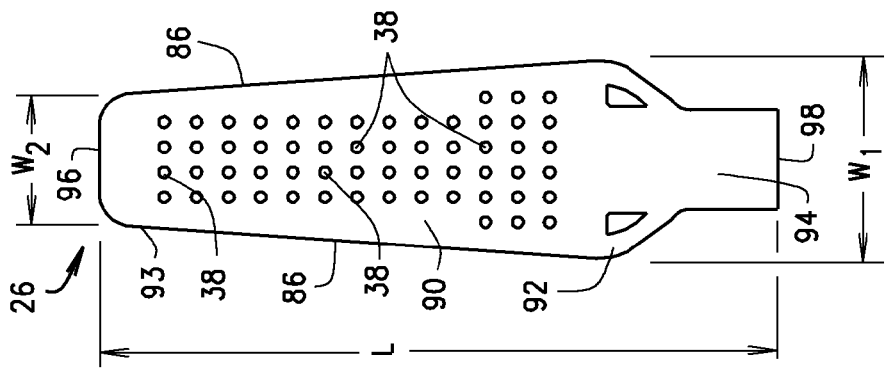
FIG. 4a is a front view of a head of the obstetrical device shown in FIG. 1, in accordance with still other various cases of the present disclosure.
Figures 4E, 4F:
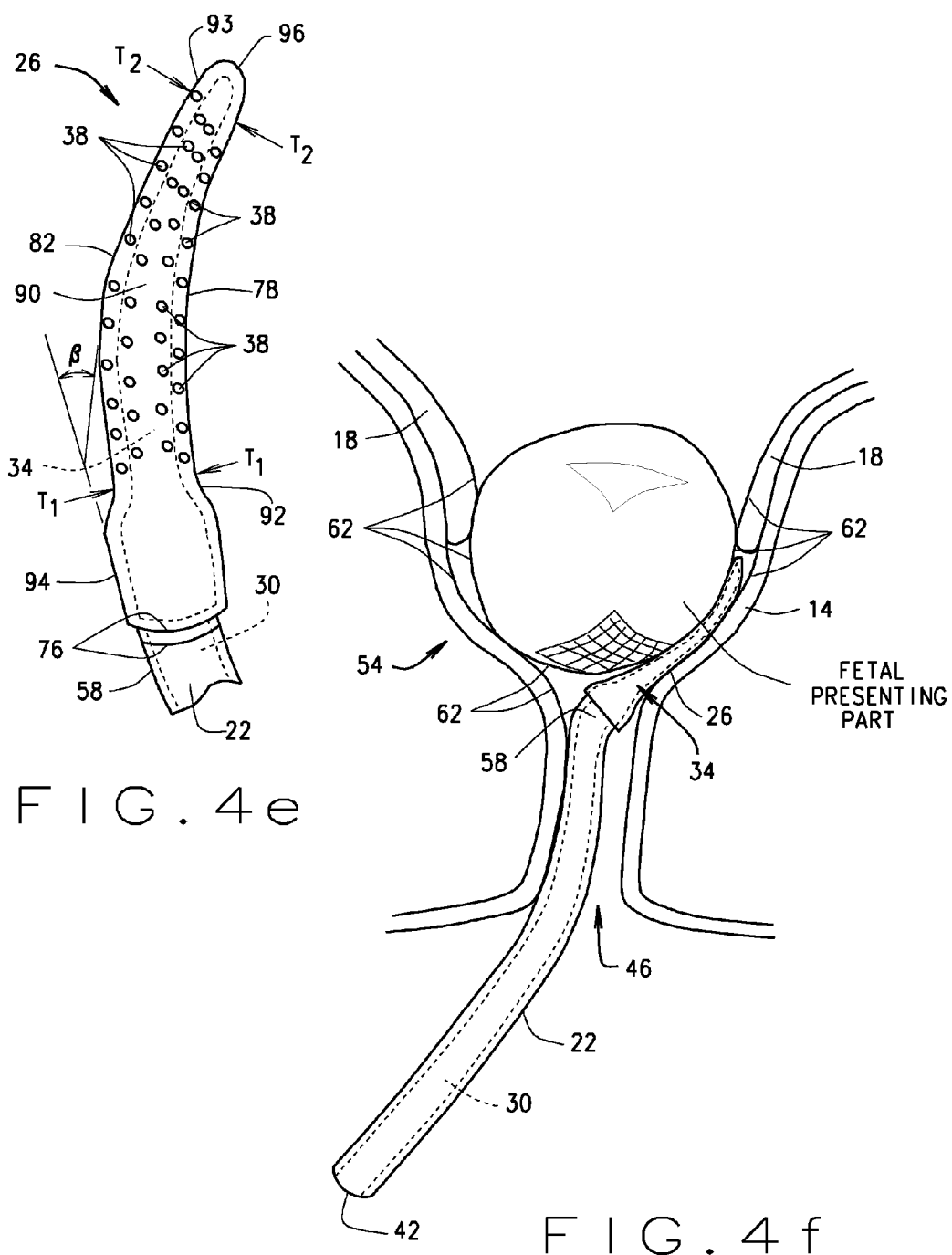
FIG. 4e is a side view of the head shown in FIGS. 4a, 4b, 4c and 4d, in accordance with various cases of the present disclosure.
FIG. 4f is an illustration of utilization of the obstetrical device shown in FIGS. 4a, 4b, 4c, 4d and 4e, in accordance with various cases of the present disclosure.

Similarly, in various cases, the width of the septum portion 90 can be slightly tapered from the neck end 92 to the distal end 93, as illustrated in FIGS. 4a and 4b. The width of the septum portion 90 can have any amount of tapering that is conducive to insertion of the head 26 between the contact surfaces 62, as described below, and allows the internal chamber 34 to remain open after such insertion. For example, in various implementations, the neck end 92 can have a width W1 of approximately 1 cm and the distal end 93 can have width W2 of 0.75 cm. Alternatively, it is envisioned that the septum portion 90 can have any other thickness and/or width configuration that is conducive to insertion of the head 26 between the contact surfaces 62, e.g., oval, polygonal, etc. For example, in various embodiments, the septum portion 90 can have a thickness that is less the width of the front and back faces 78 and 82.

Additionally, in various cases, the head 26 can be structured to have a predetermined length L from a proximal edge 98 of the neck portion 94 to the distal tip 96 that will aid the clinician in use of the BRD 10. More particularly, in various implementations, the insertion marker 76 can comprise the proximal edge 98 of the neck portion 94. Alternatively, the insertion marker 76 can be disposed on the tail 22 adjacent the proximal edge 98. Hence, in such cases, the head 26 can be fabricated to have a length L such that when the head 26 is advanced between the contact surfaces 62 to a point where the proximal edge 98 or insertion marker is substantially even with the labia of the mother, the clinician will know that the head has been advanced a desired distance between the contact surfaces 62. As described above, the length L can be any pragmatically defined length. For example, in various configurations, the length L can be between approximately 9 cm and 13 cm, e.g., 11 cm.

With reference now to FIGS. 4a, 4b, 4c, 4d, 4e, 4f and 6b, to use the BRD 10 to assist in the delivery of the fetal presenting part during a cesarean section, the head 26 is inserted into the vaginal opening 46, with or without accompaniment of the clinician's hand, such that the head 26 is inserted between the contact surfaces 62 of the fetal presenting part and the vagina 14 and/or the cervix 18. The head 26 is advanced between contact surfaces 62 until the suction holding the fetal presenting part in contact with the vagina 14 and/or the cervix 18 is broken, or until the head 26 has been advanced a desired distance, e.g., advanced until the proximal edge 98 of the head neck portion 94 or the insertion marker 76 is substantially even with the labia of the mother, at which point it is envisioned that the suction will be significantly reduced or removed.

As described above, the suction will be broken, or removed, via air flowing from the proximal end 42 of the tail 22, through the tail internal lumen 30, into the head internal chamber 34 and exiting the head internal chamber 34, via the apertures 38, into the contact area between the contact surfaces 62. More particularly, once the head 26 is inserted between the contact surfaces 62, the suction existing between the contact surfaces 62 will cause air to be drawn into the proximal end 42 of the tail 22, through the tail internal lumen 30, into the head internal chamber 34 and exit the head internal chamber 34 through the apertures 38, into the contact area between the contact surfaces 62. Hence, as described herein, providing air near and/or into the contact area, the suction pressure between the contact surfaces 62 is significantly reduced or removed, whereafter the fetal presenting part can be easily separated from the vagina 14 and/or cervix 18, thereby allowing easy delivery of the neonate.

Figure 5:
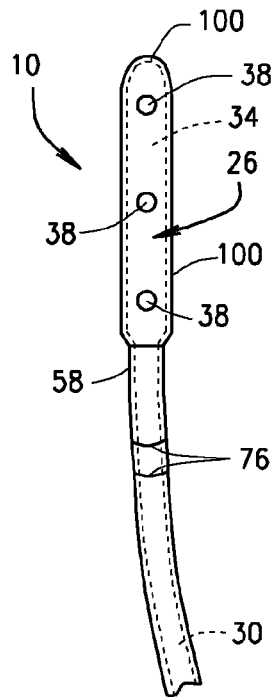
FIG. 5 is a front view of a head of the obstetrical device shown in FIG. 1, in accordance with still other various cases of the present disclosure.

Referring now to FIG. 5, in various cases, the head 26 can comprise an elongated, flexible, non-collapsible hollow structure that is detachably coupled to, or substantially permanently affixed to, the distal end 58 of the tail 22. In such cases, the head 26 can include a plurality of the apertures 38 disposed along the length of the sidewall of the head 26. In such cases, function and use of the BRD 10 is substantially the same as that described above with reference to FIGS. 2a, 2b, 2c 3a, 3b, 3c, 3d and 3e. Particularly, the head 26 is inserted into the vaginal opening 46, with or without accompaniment of the clinician's hand, such that a distal end 100 of the head 26 is placed near or in contact with the fetal presenting part. More specifically, the head 26 is advanced until the suction holding the fetal presenting part in contact with the vagina 14 and/or the cervix 18 is broken, or until the head 26 has been advanced a desired distance, e.g., advanced until the insertion marker 76 is substantially even with the labia of the mother. At which point, it is envisioned that the suction will be significantly reduced or removed, whereafter the fetal presenting part can be easily separated from the vagina 14 and/or cervix 18, thereby allowing easy delivery of the neonate.

Figure 6A:
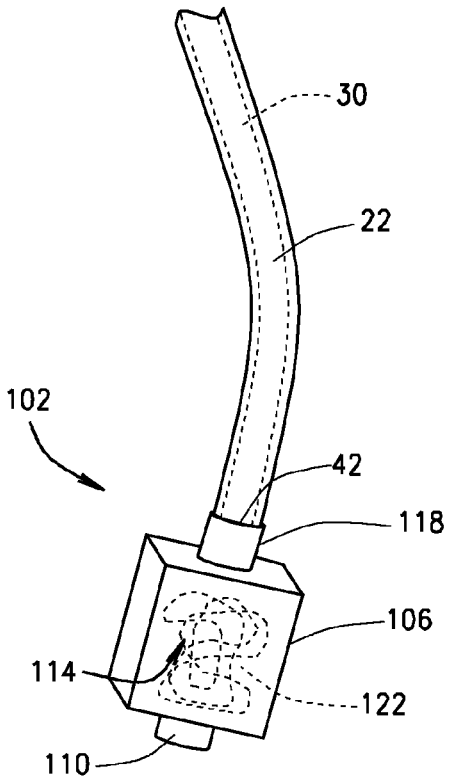
FIG. 6a is an illustration of a tail of the obstetrical device shown in FIG. 1 including a filtration device, in accordance with various cases of the present disclosure.

Referring now to FIGS. 6a and 6b, in various cases, the BRD 10 can be structured to prevent unsanitary matter from entering the tail 22. For example, as illustrated in FIG. 6a, in various cases, the BRD 10 can include an air filtration device 102 disposed at or near the proximal end 42 of the tail 22. The air filtration device 102 is structured and operable to prevent contamination of the mother's pelvis due to unsanitary matter near the vaginal opening being sucked through the tail 22 and head 26 and expelled through the head apertures 38 when the suction holding the fetal presenting in contact with vagina 14 and/or the cervix 18 is broken, as described above.

For example, in various cases, the filtration device 102 can include a hollow body 106 having an air inlet port 110 that leads to an internal cavity 114 of the body 106 and an air outlet port 118 that also leads to the internal cavity 114 and is connectable at or near the tail proximal end 42 such that it is fluidly connected to the internal lumen 30 of the tail 22. The filtration device 102 further includes a filtration membrane 122 disposed within the internal cavity 114. The filtration membrane 122 can be constructed of any coarse-air filtration material suitable to prevent unsanitary matter from flowing into the internal lumen 30 of the tail 22 while allowing adequate air flow through the filtration device body 106, and hence, through the tail 22 and head 26, to brake the suction between the contact surfaces 62, as described above. For example, in various cases, the filtration membrane can comprise a nylon mesh material. It is envisioned that the filtration device body 106 can have any suitable shape, e.g., cubical, cylindrical, pyramidal, etc., and remain within the scope of the present disclosure.

Additionally, as illustrated in FIG. 6b, in various other cases, the BRD tail 22 can be curved or bent so that the proximal end 42 will extend away from the operating table, e.g., upward. Accordingly, the proximal end 42 will be positioned away from any unsanitary matter that may be on the operating table near the vaginal opening 46.

Figure 7:
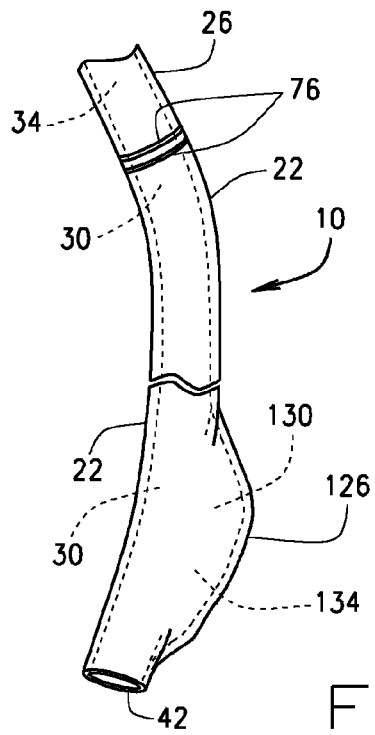
FIG. 7 is an illustration of a tail of the obstetrical device shown in FIG. 1 including an unsanitary matter collection device, in accordance with various cases of the present disclosure.

Referring now to FIG. 7, in various cases, the BRD 10 can include an unsanitary matter trap 126 that includes an internal reservoir 130 that is fluidly connected to the internal lumen 30 of the tail 22. The unsanitary matter trap 126 is structured and operable to prevent unsanitary matter from entering the head 26 of the BRD device 10. In such cases, the tail 22 includes an opening 134 in the tail sidewall that is fluidly connected to the trap internal reservoir 130 and the tail internal lumen 30. In various implementations, the opening 134 can comprise a neck-like port formed in, and extending externally away from, the tail sidewall to which the trap 126 can be connected or affixed.

Additionally, in various implementations, the tail opening 134 and trap 126 are disposed near the proximal end 42 of the tail 22 and the trap 126 is structured and operable to trap, or collect, unsanitary matter that may enter the tail 22 during use of the BRD 10. Specifically, during use, the BRD 10 is positioned and oriented such that the trap 126 is located under, or hangs down from, the proximal end portion of the tail 22. Therefore, if any unsanitary matter enters, i.e., is drawn into, the tail 22 as the suction between the contact surfaces 62 is broken, gravitational forces will cause the unsanitary matter to fall into the trap internal reservoir 130 as the unsanitary matter travels through the tail internal lumen 30. Hence, the unsanitary matter will be collected in trap internal reservoir 130 and not travel through the length of the tail internal lumen 30 to the head internal chamber 34, where it could contaminate the mother's pelvis.

The unsanitary matter trap 126 can comprise any container type device that can be affixed to or removably connected to the BRD tail 22 and is suitable for collecting the unsanitary matter as described above. For example, in various implementations, the trap 126 can comprise a sterile non-collapsible a medical-grade PVC, silicon or polyurethane based polymer (or any other suitable material or composite) container or reservoir that is integrally formed with tail 22 or is connectable to the tail 22, via a neck-like port formed in, and extending externally away from, the tail sidewall. Or, in other cases, the trap can comprises a sterile plastic, or other suitable material, bag that is integrally formed with tail 22 or is connectable to the tail 22, via a neck-like port formed in, and extending externally away from, the tail sidewall.

Hence, the present disclosure describes various cases of the BRD 10 and methods of utilizing the BRD 10 to assist in the delivery of a well applied fetal presenting part during a cesarean section. Moreover, the BRD 10, as described here, provides a means for easy and safe delivery of the well applied fetal presenting part with minimum contact and force being applied to the fetal presenting part by the clinician. Hence, the BRD 10 is structured and operable to greatly reduce the amount of force previously applied to the fetal presenting part and necessary to facilitate delivery of a neonate with a well applied fetal presenting part. Thus, the BRD 10 can eliminate, or greatly decrease, both maternal and fetal trauma that previously could occur during delivery as a result of such forces.

The description herein is merely exemplary in nature and, thus, variations that do not depart from the gist of that which is described are intended to be within the scope of the teachings. Such variations are not to be regarded as a departure from the spirit and scope of the teachings. Moreover, while specific cases have been described herein, it will be understood that the present disclosure is capable of further modifications. This patent application is intended to cover any variations, uses, or adaptations of the described subject matter following, in general, the principles of the present disclosure and including such departures from the present disclosure as come within known or customary practice within the art to which the present disclosure pertains and as may be applied to the essential features herein before set forth and as follows in scope of the appended claims.

What is claimed is:

1. An obstetrical device for assisting a cesarean section delivery of a neonate having a fetal presenting part well seated within the mother's pelvis, said device comprising:
   a hollow tail having an internal lumen extending the length of the tail; and
   a hollow tongue-shaped head disposed on a distal end of the tail, the head comprising a sterile, non-collapsible, curved structure having a hollow neck portion and an elongated hollow tongue-shaped septum portion extending from the neck portion, the hollow neck portion and the hollow tongue-shaped septum portion defining an internal chamber of the head that is fluidly connected to the tail internal lumen, the tongue-shaped septum portion comprising:
      a broad, elongated concave front face including a plurality of apertures arrayed therein;
      an opposing broad, elongated convex back face including a plurality of apertures arrayed therein; and
      a plurality of sides connecting the front and back faces such that the septum portion is structured to have a broad, elongated tongue shape, wherein the front and back faces have a width that is greater than a height of the sides such that the tongue-shaped septum portion is structured to have:
         a curvature that is complementary to a curvature of an area of contact between the fetal presenting part and at least one of the mother's vagina and cervix; and
         a thickness that is less than the width of the front and back faces such that the tongue-shaped septum portion can be inserted into the area of contact between the fetal presenting part and the at least one of the mother's vagina and cervix,
   whereby air, via the tail internal lumen, the head internal chamber and the at least one aperture of the head, is drawn into the head and directed into the area of contact between the fetal presenting part and the at least one of the mother's vagina and cervix to release a suction formed between the fetal presenting part and the at least one of the mother's vagina and cervix so that the well seated fetal presenting part can be easily separated from the at least one of the vagina and the cervix.

2. The device of claim 1 further comprising an insertion marker disposed on a distal end portion of the tail, the insertion marker operable to indicate when the head has been advanced into the vaginal opening a desired distance such that the head is positioned between the fetal presenting part and the at least one of the mother's vagina and cervix.

3. The device of claim 1, wherein the tail comprises a sterile, non-collapsible tube and the head comprises a distal end portion of the tube, the head structured and operable to be positioned, adjacent or in contact with the fetal presenting part to thereby provide air into the area between the fetal presenting part and the at least one of the mother's vagina and cervix to reduce or release the suction formed between the fetal presenting part and the at least one of the mother's vagina and cervix.

4. The device of claim 1, wherein the head comprises a sterile, non-collapsible structure disposed on the distal end of the tail and includes a hollow neck portion and a flared hollow abutment portion extending from the neck portion, the abutment portion having a distal face and including the one or more apertures, the head is structured and operable to be positioned such that the distal face is adjacent or in contact with the fetal presenting part to thereby provide air into the area at least one of near and between the contact surfaces to reduce or release the suction formed between the contact surfaces.

5. The device of claim 4, wherein the head is structured such that abutment portion extends at angle from the neck portion such that the head is ergonomically structured to provide ease and comfort in holding by a clinician during the insertion.

6. The device of claim 1, wherein the head is structured to have a predetermined length from a proximal edge of the neck portion to a distal tip of the septum portion that will indicate that the head is inserted a desired distance between the fetal presenting part and the at least one of the mother's vagina and cervix when the proximal edge of the neck is substantially even with the mother's labia.

7. The device of claim 1 further comprising an air filtration device disposed at a proximal end of the tail, the air filtration device structured and operable to prevent unsanitary matter from entering the tail of the device.

8. The device of claim 1 further comprising an unsanitary matter trap including an internal reservoir that is fluidly connected to the internal lumen of the tail, the unsanitary matter trap structured and operable to prevent unsanitary matter from entering the head of the device.

9. An obstetrical device for assisting a cesarean section delivery of a neonate having a fetal presenting part well seated within the mother's pelvis, said device comprising:
   a hollow tail having an internal lumen extending the length of the tail;
   a hollow tongue-shaped head disposed on a distal end of the tail, the head comprising a sterile, non-collapsible, curved structure having a hollow neck portion and a hollow tongue-shaped septum portion extending from the neck portion, the hollow neck portion and the hollow tongue-shaped septum portion defining an internal chamber of the head that is fluidly connected to the tail internal lumen, the tongue-shaped septum portion comprising:
      a broad, elongated concave front face including a plurality of apertures arrayed therein;
      an opposing broad, elongated convex back face including a plurality of apertures arrayed therein; and
      a plurality of sides connecting the front and back faces such that the septum portion is structured to have a broad, elongated tongue shape, wherein the front and back faces have a width that is greater than a height of the sides such that the tongue-shaped septum portion is structured to have:
         a curvature that is complementary to a curvature of an area of contact between the fetal presenting part and at least one of the mother's vagina and cervix; and
         a thickness that is less than the width of the front and back faces such that the tongue-shaped septum portion can be inserted into the area of contact between the fetal presenting part and the at least one of the mother's vagina and cervix,
   whereby air, via the tail internal lumen, the head internal chamber and the at least one aperture of the head, is drawn into the head and directed into the area of contact between the fetal presenting part and the at least one of the mother's vagina and cervix to release a suction formed between the fetal presenting part and the at least one of the mother's vagina and cervix so that the well seated fetal presenting part can be easily separated from the at least one of the vagina and the cervix; and an insertion marker disposed on a distal end portion of the tail, the insertion marker operable to indicate when the head has been advanced into the vaginal opening a desired distance such that the head is positioned between the fetal presenting part and the at least one of the mother's vagina and cervix, wherein the head is further structured and operable to, via the tail internal lumen, the head internal chamber and the at least one aperture of the head, allow air to be drawn into the head and direct the drawn air into the area between the fetal presenting part and at least one of a vagina and a cervix of the mother, and further structured and operable to release a suction formed between the fetal presenting part and the at least one of the mother's vagina and cervix so that the well seated fetal presenting part can be easily separated from the at least one of the vagina and the cervix.

10. The device of claim 9, wherein the tail comprises a sterile, non-collapsible tube and the head comprises a distal end portion of the tube, the head structured and operable to be positioned, adjacent or in contact with the fetal presenting part to thereby provide air into the area between the fetal presenting part and the at least one of the mother's vagina and cervix to reduce or release the suction formed between the fetal presenting part and the at least one of the mother's vagina and cervix.

11. The device of claim 9, wherein the head comprises a sterile, non-collapsible structure disposed on the distal end of the tail and includes a hollow neck portion and a flared hollow abutment portion extending from the neck portion, the abutment portion having a distal face and including the one or more apertures, the head structured and operable to be positioned such that the distal face is adjacent or in contact with the fetal presenting part to thereby provide air into the area at least one of near and between the contact surfaces to reduce or release the suction formed between the contact surfaces.

12. The device of claim 11, wherein the head is structured such that abutment portion extends at angle from the neck portion such that the head is ergonomically structured to provide ease and comfort in holding by a clinician during the insertion.

13. The device of claim 9, wherein the head is structured to have a predetermined length from a proximal edge of the neck portion to a distal tip of the septum portion and wherein the insertion marker comprises the proximal edge of the neck portion, whereby the insertion marker will indicate that the head is inserted a desired distance between the fetal presenting part and the at least one of the mother's vagina and cervix when the insertion marker is substantially even with the mother's labia.

14. The device of claim 9 further comprising an air filtration device disposed at a proximal end of the tail, the air filtration device structured and operable to prevent unsanitary matter from entering the tail of the device.

15. The device of claim 9 further comprising an unsanitary matter trap including an internal reservoir that is fluidly connected to the internal lumen of the tail, the unsanitary matter trap structured and operable to prevent unsanitary matter from entering the head of the device.

16. A method for assisting a cesarean section delivery of a neonate having a fetal presenting part well seated within the mother's pelvis, said method comprising:
 inserting a tongue-shaped hollow head of an obstetrical device into a vaginal opening of the mother, the obstetrical device comprising:
  a hollow tail having an internal lumen extending the length of the tail; and
  the head extending from a distal end of the tail, the head comprising a sterile, non-collapsible, curved structure having a hollow neck portion and a hollow tongue-shaped septum portion extending from the neck portion, the hollow neck portion and the hollow tongue-shaped septum portion defining an internal chamber of the head that is fluidly connected to the tail internal lumen, the tongue-shaped septum portion comprising:
   a broad, elongated concave front face including a plurality of apertures arrayed therein;
   an opposing broad, elongated convex back face including a plurality of apertures arrayed therein; and
   a plurality of sides connecting the front and back faces such that the septum portion is structured to have a broad, elongated tongue shape, wherein the front and back faces have a width that is greater than a height of the sides such that the tongue-shaped septum portion is structured to have:
    a curvature that is complementary to a curvature of an area of contact between the fetal presenting part and at least one of the mother's vagina and cervix; and
    a thickness that is less than the width of the front and back faces such that the tongue-shaped septum portion can be inserted into the area of contact between the fetal presenting part and the at least one of the mother's vagina and cervix;
 inserting the broad, elongated tongue-shaped septum portion into the area of contact between the fetal presenting part and the at least one of the mother's vagina and cervix;
 providing a path for air to be drawn into the head, via the internal lumen of the tail, the internal chamber and the at least one aperture of the head;
 directing the drawn air into the area of contact between the fetal presenting part and the at least one of the vagina and the cervix of the mother; and
 releasing a suction formed between the fetal presenting part and the at least one of the vagina and the cervix of the mother so that the well seated fetal presenting part can be easily separated from the at least one of the vagina and the cervix.

17. The method of claim 16 further comprising advancing the head until an insertion marker disposed on a distal end portion of the tail is substantially even with the mother's labia, thereby indicating that the head has been advanced into the vaginal opening a desired distance such that the head is positioned between the fetal presenting part and the at least one of the mother's vagina and cervix.

18. The method of claim 17, wherein positioning the head between the fetal presenting part and the at least one of the mother's vagina and cervix comprises positioning the head comprising a distal end portion of the tail that comprises a sterile, non-collapsible tube, adjacent or in contact with the fetal presenting part to thereby provide air into the area between the presenting part and the at least one of the mother's vagina and cervix.

19. The method of claim 16, wherein the head comprises a sterile, non-collapsible structure disposed on the distal end of the tail and includes a hollow neck portion and a flared hollow abutment portion extending from the neck portion, the abutment portion having a distal face and including the one or more apertures, and wherein positioning the head at least one of near and between contact surfaces comprises positioning the distal face of the abutment portion adjacent or in contact with the fetal presenting part to thereby provide air into the area at least one of near and between the contact surfaces.

* * * * *

UNITED STATES PATENT AND TRADEMARK OFFICE
CERTIFICATE OF CORRECTION

PATENT NO. : 9,039,714 B2  
APPLICATION NO. : 13/016057  
DATED : May 26, 2015  
INVENTOR(S) : Breton F. Barrier and Gary F. Clark Page 1 of 1

It is certified that error appears in the above-identified patent and that said Letters Patent is hereby corrected as shown below:

In the claims

In column 14, Claim 18, line 7, insert the word --fetal-- after the word 'the' and before the word 'presenting'.

Signed and Sealed this
Eighth Day of December, 2015

Michelle K. Lee
*Director of the United States Patent and Trademark Office*